US008168841B2

(12) United States Patent
Herwig et al.

(10) Patent No.: US 8,168,841 B2
(45) Date of Patent: May 1, 2012

(54) PROCESS FOR PREPARING CYCLODODECATRIENE

(75) Inventors: Jürgen Herwig, Hünxe (DE); Wilhelm Brügging, Haltern am See (DE); Martin Roos, Haltern am See (DE); Norbert Wilczok, Mülheim (DE)

(73) Assignee: EVONIK DEGUSSA GmbH, Essen (DE)

( * ) Notice: Subject to any disclaimer, the term of this patent is extended or adjusted under 35 U.S.C. 154(b) by 364 days.

(21) Appl. No.: 11/688,505

(22) Filed: Mar. 20, 2007

(65) Prior Publication Data
US 2007/0265184 A1 Nov. 15, 2007

(30) Foreign Application Priority Data
May 10, 2006 (DE) .......... 10 2006 022 014

(51) Int. Cl.
*C07C 2/46* (2006.01)
(52) U.S. Cl. ........ 585/366; 585/365; 585/367; 585/368; 585/369; 585/370
(58) Field of Classification Search .......... 585/415–419, 585/502, 506, 507, 508, 510, 511, 512, 367, 585/365, 366, 368, 369, 370
See application file for complete search history.

(56) References Cited

U.S. PATENT DOCUMENTS

| 3,007,974 | A | | 11/1961 | Lippincott | |
|---|---|---|---|---|---|
| 3,149,173 | A | * | 9/1964 | Wittenberg et al. | 585/367 |
| 3,214,484 | A | * | 10/1965 | Wittenberg et al. | 585/367 |
| 3,243,467 | A | * | 3/1966 | Zuech | 585/369 |
| 3,381,045 | A | * | 4/1968 | Koch et al. | 585/367 |
| 3,420,899 | A | * | 1/1969 | Longiave et al. | 585/367 |
| 3,499,049 | A | * | 3/1970 | Hochmuth et al. | 585/368 |
| 3,546,309 | A | | 12/1970 | Koch et al. | |
| 3,843,738 | A | * | 10/1974 | Morikawa et al. | 585/368 |
| 3,849,371 | A | | 11/1974 | Wolford et al. | |
| 3,878,258 | A | * | 4/1975 | Rapoport et al. | 585/368 |
| 4,151,316 | A | | 4/1979 | Eckert | |
| 6,403,851 | B1 | * | 6/2002 | Wilczok et al. | 585/366 |
| 6,407,304 | B2 | | 6/2002 | Schiffer et al. | |
| 6,620,970 | B2 | | 9/2003 | Schiffer et al. | |
| 6,639,108 | B2 | | 10/2003 | Schiffer et al. | |
| 6,664,423 | B2 | | 12/2003 | Herwig et al. | |
| 6,828,449 | B2 | | 12/2004 | Herwig et al. | |
| 6,861,540 | B2 | | 3/2005 | Herwig et al. | |
| 6,927,308 | B2 | | 8/2005 | Leininger et al. | |
| 7,084,300 | B2 | | 8/2006 | Herwig et al. | |
| 7,495,129 | B2 | | 2/2009 | Balduf et al. | |
| 2004/0225168 | A1 | | 11/2004 | Herwig et al. | |
| 2007/0004903 | A1 | | 1/2007 | Hoff et al. | |
| 2009/0099059 | A1 | * | 4/2009 | Kuppert et al. | 512/8 |
| 2009/0306367 | A1 | | 12/2009 | Roos et al. | |

FOREIGN PATENT DOCUMENTS

| DE | 1140 569 | | 12/1962 |
|---|---|---|---|
| DE | 2 026 043 | | 12/1970 |
| DE | 1 768 067 | | 1/1972 |
| EP | 1 069 098 A1 | | 1/2001 |
| GB | 928812 | | 6/1963 |
| GB | 1095835 | | 12/1967 |
| WO | WO 2006051011 A1 | * | 5/2006 |

OTHER PUBLICATIONS

Lide, et al., CRC Handbook of Chemistry and Physics, 91st Edition, 2011 Internet Version.*
Lide, et al., CRC Handbook of Chemistry and Physics, D. R. Lide, ed., 91st Edition, 2011 Internet Version.*
U.S. Appl. No. 10/572,594, filed Mar. 20, 2006, Herwig, et al.
U.S. Appl. No. 11/719,164, filed May 11, 2007, Kuppert, et al.
U.S. Appl. No. 12/922,807, filed Sep. 15, 2010, Hannen, et al.
U.S. Appl. No. 12/865,018, filed Jul. 28, 2010, Hannen, et al.
U.S. Appl. No. 13/142,505, filed Jun. 28, 2011, Meier, et al.

* cited by examiner

*Primary Examiner* — In Suk Bullock
*Assistant Examiner* — Bradley Etherton
(74) *Attorney, Agent, or Firm* — Oblon, Spivak, McClelland, Maier & Neustadt, L.L.P

(57) ABSTRACT

Preparation of cyclododecatriene in a continuous or discontinuous process by trimerization of butadiene in the presence of a catalyst system and a solvent, the crude cyclododecatriene obtained being able to be isolated by means of distillation. The cyclooctadiene formed as by-product can likewise be isolated from the crude product.

14 Claims, No Drawings

US 8,168,841 B2

PROCESS FOR PREPARING CYCLODODECATRIENE

CROSS-REFERENCE TO RELATED APPLICATIONS

This application claims priority to DE (Germany) 102006022014.5, filed May 10, 2006, which is hereby incorporated by reference in its entirety.

BACKGROUND OF THE INVENTION

1. Field of the Invention

The present invention relates to a continuous and discontinuous process for preparing cyclic butadiene trimers, i.e. cyclododeca-1,5,9-triene (CDT) using a catalyst system containing nickel and/or titanium. Furthermore, the present invention relates to the abovementioned process in which cyclooctadiene (COD) and/or vinylcyclohexene (VCH) can additionally be isolated from the reaction mixture, preference being given to using a nickel-containing catalyst system in this case. The present invention also encompasses mixtures having a particular ratio of CDT to $C_{16}$-, $C_{20}$-, $C_{24}$-hydrocarbons and polymers having molecular weights up to 5000. It further encompasses mixtures having CDT as main constituent and a very small proportion of chlorocyclododecatriene (Cl-CDT). These mixtures can be obtained by the process of the invention.

2. Description of Related Art

A large number of patents and publications are concerned with processes or experiments for preparing cyclic dimers and trimers of conjugated dienes, in particular butadiene.

The formation of cyclododecatriene in the presence of a titanium catalyst has been described, for example, in JP-A-2003064011. Here, the reaction was carried out using a catalyst system composed of titanium tetrachloride, 4,4'-dichlorobenzophenone, dimethyl sulfoxide and diethylaluminum sesquichloride at a temperature of 40° C. After the reaction was complete, the mixture was admixed with MeONa/MeOH and washed with aqueous trisodium citrate to remove the titanium and aluminum from the organic reaction mixture. JP-A-02083339 describes a similar process, likewise using DMSO. The presence of the high-boiling DMSO as additive is disadvantageous for an industrial process since it has to be removed again from the reaction mixture.

FR-A-1393071 describes the formation of CDT using titanium and aluminum as catalyst system. As titanium catalyst, use was made of $Ti(OR)_4$, where R is an aliphatic $C_3$-$C_4$-alkyl radical, and $AlR'X_2$ or $AlRK'_2X$, where R' is a straight-chain or branched $C_1$-$C_{18}$-alkyl radical or a $C_1$-$C_6$-cycloalkyl radical or a $C_1$-$C_{10}$-aralkyl radical and X is Cl or Br, was used as aluminum catalyst. The reaction described in FR1393071 requires very long reaction times of 18 hours and is therefore unsuitable for industrial use. Furthermore, no yields are reported in the French patent.

U.S. Pat. No. 3,499,049 describes a method of accelerating the catalytic trimerization of butadiene by addition of water to the reaction mixture. This process has the disadvantage that the amount of undesirable by-products is too high. Particularly in continuous operation, the yields of CDT of 83% or 62% achieved in U.S. Pat. No. 3,499,049 are not sufficient for industrial use.

GB 928,812 likewise describes a process for preparing cyclododecatriene using specific catalysts containing a semipolar double bond in the molecule. The best results are achieved using DMSO, which as indicated above leads to disadvantages in the work-up of the reaction mixture.

DE 1140569 discloses the formation of dimers and trimers of 1,3-diolefins by means of nickel or cobalt catalyst systems. The catalyst systems additionally contain organometallic compounds and compounds having electron donor properties. The process of DE 11 40 569 requires the use of dry solvents, which is associated with a considerable technical outlay and thus economic disadvantages.

In the industrial trimerization of butadiene to cyclododecatriene (CDT), homogeneous catalysts are used and the reaction is carried out in a continuous process in one or more stirred vessels. Parts of the reaction mixture are taken off continuously from the reaction mixture. During the work-up, unreacted starting material is recovered and is returned together with fresh butadiene to the circuit. When parts of the reaction mixture are taken off, parts of the catalyst are likewise taken from the reaction mixture. As a result, the concentration of the catalyst in the reaction mixture drops and the catalyst taken off has to be replaced by fresh catalyst in order to keep the catalyst concentration constant.

Before the work-up of the material taken off from the reactor, the catalyst taken off has to be destroyed. Many polar solvents are used for this purpose. Apart from water, Ube Industries utilizes, for example, ammonium hydroxide solutions (JP-A-05-070377, JP 06-25438). Various alcohols can likewise be utilized (JP-A-07-625439, JP 07-625396). In particular, methanol (JP-A-07-442496) and methanol/HCl (DE-A-19 42 729) are preferably used.

The decomposition of the catalyst can also be carried out by means of acetone (JP-A-04-301345) or by means of a suspension of calcium oxide in water NL-A-6 603 264). Ube Industries has additionally reported that the yield of CDT drops when water is used to decompose the catalyst.

BRIEF SUMMARY OF THE INVENTION

Starting out from the abovementioned prior art, it was therefore an object of the present invention to provide a process for preparing cyclododecatriene (CDT) in high yields and with a low amount of polymeric by-products. A further object was to provide a process in which the amount of $C_8$ dimers is low. Finally, a further object was to provide a process which, particularly in the case of nickel-catalyzed systems, allows not only large amounts of CDT but also cyclooctadiene to be isolated.

These objects and further objects which are not explicitly mentioned and their achievement are disclosed in the following description and also the examples and claims.

DETAILED DESCRIPTION OF THE PREFERRED EMBODIMENTS

It has now surprisingly been found that transition metal complexes of nickel and/or of titanium can trimerize butadiene to CDT with high selectivity. To be able to achieve this high selectivity, it is necessary for a compound containing an element of main group 5 of the Periodic Table and a suitable solvent system to be used. Furthermore, it has been found that the reaction temperature should be below 140° C. in the case of nickel-catalyzed systems and should be below 80° C. in the case of titanium-catalyzed systems.

The invention accordingly provides a process for preparing CDT from butadiene in the presence of a catalyst system which is defined in the appended claims and is specified in more detail by the following description. The present invention provides, in particular, a continuous and/or discontinuous process for preparing cyclododecatriene by reaction of butadiene in the presence of a solvent, at least one catalyst system containing nickel and/or titanium and at least one organometallic compound to form a crude cyclododecatriene, wherein
- a compound containing at least one element of main group 5 of the Periodic Table of the Elements is added to the catalyst system,
- the solvent contains, before the addition of the catalyst component, 10-1000 ppm of a polar component of the general formula HO—R, where R is selected from the group consisting of branched and unbranched $C_1$-$C_{18}$-alkyl, $C_1$-$C_8$-cycloalkyl, $C_1$-$C_{18}$-aryl, $C_1$-$C_{18}$-aralkyl and H, and
- the reaction temperature is less than or equal to 140° C. in the case of a nickel-containing catalyst system and less than or equal to 80° C. in the case of a titanium-containing catalyst system.

The present invention likewise provides a process in which not only CDT but also COD and/or VCH can be isolated from the reaction mixture.

The invention further provides mixtures obtainable by the process of the invention, wherein the ratio of cyclododecatriene to higher oligomers, e.g. $C_{16}$-, $C_{20}$-, $C_{24}$-hydrocarbons, determined by means of gas chromatography (DB1 column), and/or polymers having molecular weights up to 5000 is greater than or equal to 10:1, preferably greater than 15:1, particularly preferably greater than 20:1. Preference is also given to the ratio of cyclododecatriene to higher oligomers being less than 60:1 and particularly preferably less than 50:1. The ratios described above include all intermediate subranges and values.

The present invention likewise provides mixtures, wherein the amount of chlorocyclododecatriene in the crude cyclododecatriene and/or in the purified cyclododecatriene is not more than 100 ppm, preferably 0.01-80 ppm, particularly preferably from 0.1 to 70 ppm, very particularly preferably from 1 to 50 ppm and from 1 to 30 ppm. The values described above include all intermediate subranges and values.

These mixtures according to the invention can preferably contain trans,trans,trans-CDT in the case of nickel as catalyst and preferably contain cis,trans,trans-CDT in the case of titanium as catalyst.

As is confirmed in the following, the process of the invention makes it possible to prepare trimers of butadiene, in particular cyclododeca-1,5,9-triene (CDT) with high selectivity and in high yields, with very short reaction times being required. Furthermore, the amount of polymeric by-products has been able to be reduced by means of the process of the invention. Thus, the process of the invention leads to product mixtures in which the ratio of CDT to higher oligomers and/or to polymers is optimized. Finally, the process of the invention is suitable for preparing crude CDT mixtures or purified CDT having a proportion of Cl-CDT of less than 100 ppm.

Without being tied to a particular theory, the surprising and advantageous effects can be explained by a synergistic action of the compound containing an element of main group 5 of the Periodic Table, the catalysts and the ROH component. In particular, addition of a compound containing an element of main group 5 of the Periodic Table results in formation of a significantly smaller amount of polymeric by-products and of Cl-CDT, the space-time yield and the selectivity of the reaction being very high at the same time.

Starting materials for the catalyst systems of the process of the invention are preferably commercially available nickel(II) and/or titanium(IV) compounds. Particular preference is given to $TiX_4$, where X=F, Cl, Br, I or a mixture thereof. Very particular preference is given to nickel acetylacetonate and titanium tetrachloride.

The reaction is carried out at catalyst concentrations of from 0.01 to 40 mmol/l, preferably from 0.05 to 10 mmol/l, based on nickel or titanium. The values described above include all intermediate subranges and values.

The organometallic compounds comprise at least one element of main groups 1 to 3 of the Periodic Table of the Elements, preferably aluminum. Particular preference is given to ethoxydiethylaluminum and ethylaluminum sesquichloride.

The ratio of organometallic compound to the nickel-containing catalyst is selected so that the molar ratio of nickel to the organometallic compound is from 1:3 to 1:10, preferably from 1:3 to 1:6. The reaction temperature is less than or equal to 140° C., preferably from 60 to 140° C., particularly preferably 60-120° C. The molar ratios described above and temperature ranges described above include all intermediate subranges and values.

In the case of titanium-catalyzed reactions, the molar ratio of titanium to organometallic compound is from 1:10 to 1:60, preferably from 1:10 to 1:40. The reaction temperature is less than or equal to 80° C., preferably from 20 to 80° C., particularly preferably 30-75° C. and very particularly preferably from 30 to 70° C. The molar ratios described above and temperature ranges described above include all intermediate subranges and values.

The compounds containing at least one element of main group 5 of the Periodic Table of the Elements which are part of the catalytic system preferably contain one or more nitrogen or phosphorus atoms. Particular preference is given to ammonia, amines, pyridines and pyridones. Very particular preference is given to ammonia and primary and secondary amines such as $C_1$-$C_8$-alkylamines and dialkylamines. The compounds containing at least one element of main group 5 of the Periodic Table of the Elements can be added as pure substance or in the form of organic or aqueous solutions. The concentration of the element of main group 5 of the Periodic Table of the Elements is preferably 10-200 ppm, particularly preferably 10-100 ppm, very particularly preferably 10-90 ppm and in particular 30-90 ppm. The concentrations described above include all intermediate subranges and values.

The solvents utilized in the process of the invention encompass saturated and unsaturated solvents, nonpolar aprotic solvents, aliphatic and aromatic hydrocarbons and also mixtures thereof. Nonlimiting examples are toluene, benzene, xylene, hexanes, octanes, vinylcyclohexene, cyclohexanes, cyclooctanes, cyclooctadienes, cyclododecanes, cyclododecatriene and mixtures thereof. The solvent preferably has a concentration of from 1 to 99% by weight, particularly preferably from 5 to 95% by weight, in the mixture at the end of the reaction or during the reaction if the reaction is carried out continuously. The solvent has to contain a small amount of a polar component of the general formula HO—R, where R is selected from the group consisting of branched and unbranched aryl, $C_1$-$C_{18}$-alkyl, $C_1$-$C_{18}$-cycloalkyl, $C_1$-$C_{18}$-aryl, $C_1$-$C_{18}$-aralkyl and H, the carbon atoms of the alkyl cycloalkyl, aryl and aralkyl radicals being able to be replaced by a heteroatom, in particular O, N or S, or the carbon atoms being able to bear hydroxyl groups, amino groups and/or halogen atoms. R is particularly preferably selected from the group consisting of methyl, ethyl, propyl, isopropyl, butyl, isobutyl, tert-butyl and H. The solvent preferably contains from 10 to 500 ppm or from 15 to 250 ppm of the polar component. The concentrations described above described above include all intermediate subranges and values.

The process of the invention can be operated in the pressure range 1-20 bar, preferably from 1 to 10 bar. The operating pressure can be set via the reaction temperature and/or injection of inert gases, preferably nitrogen. The pressure ranges described above include all intermediate subranges and values.

The process of the invention can be operated continuously or discontinuously, the addition of the individual components preferably being carried out in the following order:

firstly the solvent including polar component, then at least one organometallic compound, then at least one titanium- and/or nickel-containing compound, then at least one compound containing an element of main group 5 of the Periodic Table and then butadiene.

firstly the solvent including polar component, then at least one titanium- and/or nickel-containing compound, then at least one organometallic compound, then at least one compound containing an element of main group 5 of the Periodic Table and then butadiene.

Firstly the solvent including polar component, then at least one compound containing an element of main group 5 of the Periodic Table, then at least one titanium- and/or nickel-containing compound, then at least one organometallic compound and then butadiene.

The addition of the individual components can be effected with or without a time delay. It is possible to add all components in a short time and subsequently to stir the mixture until the reaction is complete. However, it is also possible to add the individual components over a longer period of time, as a result of which a shorter subsequent stirring time is required. Combinations of the two variants are likewise possible. The further stirring is preferably carried out at the same temperature at which the individual components have been added. The butadiene is preferably added with the temperature being kept constant at a particular value.

The reaction is preferably continued until >90%, particularly preferably >95%, of the butadiene have, according to analysis by gas chromatography, been reacted.

Instead of stirring, it is possible to employ any type of mixing known to those skilled in the art, e.g. by means of circulating pumps or other types of flow mixers.

The CDT prepared according to the invention or the mixtures according to the invention containing CDT are preferably processed further to produce lactams, e.g. laurolactam, to produce polyamides, e.g. polyamide 12, or to produce dicarboxylic acids, e.g. dodecanedioic acid, or used in fragrances and flame retardants.

Lactams, polyamides and dicarboxylic acids may be produced using cyclododecatriene using methods known in the art. Such methods are also incorporated by reference to *Ullmann's Encyclopedia of Chemistry*, Wiley-VCH Verlag GmbH & Co. KGaA, Weinheim (2005): "Cyclododecatriene, Cyclooctadiene, and 4-Vinylcyclohexene" by Thomas Schiffer and Georg Oenbrik; "Dicarboxylic Acids, Aliphatic" by Boy Cornils and Peter Lappe"; and "Cyclododecanol, Cyclododecanone, and Laurolactam" by Thomas Shiffner and Georg Oenbrink.

The following examples serve to illustrate the invention without restricting it in any way.

EXAMPLES

Comparative Example 1

The reaction of butadiene to form cyclododecatriene is carried out in a three-stage cascade of stirred vessels (volume of each reactor: 10 liters). The temperature is maintained at 60° C. by cooling of the double wall. Reactors 1 and 2 are additionally provided with external cooling circuits to enable the heat of reaction to be removed. The pressure in the reactor 3 is regulated by means of a valve to from 2 to 3 bar, and the pressures in the preceding reactor are slightly higher.

In the steady state, the feed to reactor 1 comprises 1.5 kg/h of 1,3-butadiene, 0.5 kg/h of benzene, 0.34 g/h of $TiCl_4$ (dissolved in benzene) and 7.9 g/h of ethylaluminum sesquichloride (EASC) (dissolved in benzene). Butadiene and benzene were dried beforehand by means of a molecular sieve, so that a water content of about 15 ppm is established in reactor 1.

The conversion of butadiene at the end of the cascade is more than 95%.

The selectivity to CDT is 87.2%, that to the $C_8$ isomers is 5.4%, that to higher oligomers ($C_6$, $C_{20}$ and $C_{24}$) is 3% and that to polybutadiene is 4.4%.

After work-up by distillation to give a CDT having a purity of greater than or equal to 99%, the product contains 250 ppm of chloride (bound as monochloro-CDT).

Comparative Example 2

The experiment was carried out as in comparative example 1, but the moisture content in the reactor is set to 110 ppm by conditioning of butadiene and benzene with water.

The conversion of butadiene at the end of the cascade is more than 99%.

The selectivity to CDT is 90.2%, that to the $C_8$ isomers is 3.9%, that to higher oligomers is 2.8% and that to polybutadiene is 3.1%.

After work-up by distillation to give a CDT having a purity of greater than or equal to 99%, the product contains 230 ppm of chloride (bound as monochloro-CDT).

Comparative Example 3

The experiment was carried out as in comparative example 1, but the reaction was carried out under water-free conditions. An ammonia content of 85 ppm was set by means of a separate metered addition.

The conversion of butadiene at the end of the cascade is more than 99%.

The selectivity to CDT is 89.8%, that to the $C_8$ isomers is 4.6%, that to higher oligomers is 2.1% and that to polybutadiene is 3.5%.

After work-up by distillation to give a CDT having a purity of greater than or equal to 99%, the product contains 60 ppm of chloride (bound as monochloro-CDT).

Example 1

According to the Invention

The experiment was carried out as in comparative example 1, but the moisture content in the reactor 1 is set to 115 ppm by conditioning of butadiene and benzene with water. In addition, an ammonia content of 80 ppm was set by means of a separate metered addition.

The conversion of butadiene at the end of the cascade is more than 99%.

The selectivity to CDT is 93.7%, that to the $C_8$ isomers is 2.9%, that to higher oligomers is 1.1% and that to polybutadiene is 2.3%.

After work-up by distillation to give a CDT having a purity of greater than or equal to 99%, the product contains less than 10 ppm of chloride (bound as monochloro-CDT).

Example 2

According to the Invention

The experiment was carried out basically as in example 1; a moisture content of 105 ppm and an ammonia content of 80 ppm are set in reactor 1. However, the operation of the stirrer is dispensed with, i.e. the mixing in reactors 1 and 2 is effected only by means of the pumped circuits.

The conversion of butadiene at the end of the cascade is more than 98.5.

The selectivity to CDT is 92.2%, that to the $C_8$ isomers is 3.1%, that to higher oligomers is 1.7% and that to polybutadiene is 3%.

After work-up by distillation to give a CDT having a purity of greater than or equal to 99%, the product contains less than 10 ppm of chloride (bound as monochloro-CDT).

Example 3

According to the Invention

The experiment was carried out basically as in example 1; a moisture content of 120 ppm and an ammonia content of 75 ppm are set in reactor 1. However, a mixture of COD and VCH (50:50) is used instead of benzene as solvent.

The conversion of butadiene at the end of the cascade is more than 99%.

The selectivity to CDT is 93.3%, that to the $C_8$ isomers is 3.2%, that to higher oligomers is 0.9% and that to polybutadiene is 2.6%.

After work-up by distillation to give a CDT having a purity of greater than or equal to 99%, the product contains about 30 ppm of chloride (bound as monochloro-CDT).

Example 4

According to the Invention

The experiment was carried out basically as in example 1; a moisture content of 110 ppm and an ammonia content of 85 ppm are set in reactor 1. Reactor 1 is maintained at 46° C. and reactor 2 is maintained at 53° C. by means of improved cooling.

The conversion of butadiene at the end of the cascade is more than 98%.

The selectivity to CDT is 94.2%, that to the $C_8$ isomers is 2.8%, that to higher oligomers is 1.2% and that to polybutadiene is 1.8%.

After work-up by distillation to give a CDT having a purity of greater than or equal to 99%, the product contains less than 10 ppm of chloride (bound as monochloro-CDT).

The invention claimed is:

1. A process for preparing cyclododecatriene, comprising:
   reacting butadiene in a solvent, in the presence of at least one catalyst system to form a crude cyclododecatriene mixture,
   wherein
   the process is continuous,
   the at least one catalyst system comprises:
      one selected from the group consisting of nickel, titanium and a mixture thereof;
      ethoxydiethylaluminum or ethylaluminum sesquichloride; and
      10 to 200 ppm by mass of the reaction mixture of at least one compound selected from the group consisting of ammonia, a $C_{1-8}$ alkyl primary amine and a $C_{1-8}$ dialkyl secondary amine;
   the solvent comprises, before the addition of the at least one catalyst system, 10-1000 ppm by mass of a polar component of the general formula HO—R, where R is selected from the group consisting of branched and unbranched $C_1$-$C_{18}$-alkyl, $C_1$-$C_{18}$-cycloalkyl, $C_1$-$C_{18}$-aryl, $C_1$-$C_{18}$-aralkyl and H, and
   a temperature of the butadiene reaction is less than or equal to 140° C. in the case of a nickel catalyst system and less than or equal to 80° C. in the case of a titanium catalyst system.

2. The process of claim 1, wherein
the catalyst system comprises nickel and the nickel is present as nickel acetylacetonate.

3. The process of claim 1, wherein
the catalyst system comprises titanium and the titanium is present as $TiX_4$, where X=F, Cl, Br, I or a mixture thereof.

4. The process of claim 1, wherein
the reaction temperature is from 60 to 120° C. in the case of a nickel catalyst system and from 30 to 75° C. in the case of a titanium catalyst system.

5. The process of claim 1, wherein
the catalyst comprises ammonia.

6. The process of claim 1, wherein
the catalyst comprises a $C_{1-8}$ primary amine.

7. The process of claim 1, wherein
the solvent is an aromatic or aliphatic solvent or a mixture thereof.

8. The process of claim 1, wherein
a concentration of nickel or titanium of the catalyst system in the reaction mixture is from 0.01 to 40 mmol/l.

9. The process of claim 1, wherein
an order of addition of reaction mixture components is:
firstly the solvent including polar component,
then the ethoxydiethylaluminum or ethylaluminum sesquichloride,
then the at least one titanium- and/or nickel catalyst,
then the at least one compound comprising an element of main group 5 of the Periodic Table, and
then butadiene.

10. The process of claim 1, wherein
an order of addition of reaction components is
firstly the solvent comprising a polar component,
then the at least one titanium- and/or nickel catalyst,
then the ethoxydiethylaluminum or ethylaluminum sesquichloride,
then the at least one compound comprising an element of main group 5 of the Periodic Table,
and then butadiene.

11. The process of claim 1, wherein
the catalyst system comprises nickel and a molar ratio of nickel to aluminum is from 1:3 to 1:6.

12. The process of claim 1, wherein
the catalyst system comprises titanium and a molar ratio of titanium to aluminum is from 1:10 to 1:60.

13. The process of claim 1, further comprising:
isolating cycloocta-1,5-diene (COD) and/or vinylcyclohexene (VCH) from the crude cyclododecatriene.

14. A composition obtained by the process of claim 1.

* * * * *